(12) United States Patent
Hersh

(10) Patent No.: US 6,228,347 B1
(45) Date of Patent: *May 8, 2001

(54) ANTIOXIDANT GEL FOR GINGIVAL CONDITIONS

(75) Inventor: Theodore Hersh, Atlanta, GA (US)

(73) Assignee: Thione International, Inc., Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/163,101

(22) Filed: Sep. 29, 1998

Related U.S. Application Data

(63) Continuation-in-part of application No. 08/982,058, filed on Dec. 1, 1997, now Pat. No. 5,922,346.

(51) Int. Cl.$^7$ ............................... A61K 9/68; A61K 7/16; A61K 7/18; A61K 9/28; A61K 9/127
(52) U.S. Cl. ............................... 424/49; 424/48; 424/52; 424/401; 424/440; 424/441; 424/450; 424/464; 424/702; 514/458; 514/474; 514/725; 514/900; 514/902; 514/904; 514/944

(58) Field of Search ........................... 424/48, 49, 52, 424/401, 440, 441, 450, 464, 702; 514/458, 474, 725, 900, 902, 904, 944

(56) References Cited

U.S. PATENT DOCUMENTS

| | | | | |
|---|---|---|---|---|
| 5,032,384 | * | 7/1991 | Yeh et al. | 424/49 |
| 5,378,461 | * | 1/1995 | Neigut | 424/94.1 |
| 5,626,883 | * | 5/1997 | Paul | 424/605 |
| 5,667,791 | * | 9/1997 | Hersh et al. | 424/401 |
| 5,709,873 | * | 1/1998 | Bar-Shalom et al. | 424/422 |
| 5,906,811 | * | 5/1999 | Hersh | 424/54 |

* cited by examiner

Primary Examiner—Shelley A. Dodson
Assistant Examiner—Marina Lamm
(74) Attorney, Agent, or Firm—Malcolm B. Wittenber

(57) ABSTRACT

A gel, paste, gum or lozenge composition for oral application to human gums to prevent and reduce symptoms of gum disease. The composition includes reduced glutathione and a source of selenium.

24 Claims, No Drawings

ANTIOXIDANT GEL FOR GINGIVAL CONDITIONS

RELATED APPLICATIONS

The present application is a continuation-in-part of U.S. patent application Ser. No. 08/982,058, filed on Dec. 1, 1997, U.S. Pat. No. 5,922,346.

TECHNICAL FIELD OF THE INVENTION

The present invention deals with the combination of several synergistic antioxidants, enzymatic co-factors and amino acids in appropriate delivery vehicles forming gels, pastes, gums or lozenges. The gels, pastes, gums or lozenges are intended to be applied or taken orally to prophylactically prevent gum disease and remedially to a patient to reduce reactive oxygen and other free radical species which are causative inflammatory factors in establishing and promoting such gingival diseases.

BACKGROUND OF THE INVENTION

Dentists and other professionals involved with the science of oral hygiene have dealt with a number of symptoms or pathologies of the mouth, gum and teeth. Some of these pathologies are initiated and exacerbated through tobacco consumption, whether smoked or chewed, as smokers often suffer from leukoplakia, a white patch on the buccal mucosa. Although leukoplakia is a benign oral lesion, it has a malignant potential requiring a biopsy of the lesion to rule out cancer. Smokers also have more dental tartar (calculus) than non-smokers and often suffer from halitosis.

It is known that tooth loss can directly result from untreated destructive periodontal (gum) disease. Further, acute necrotizing ulcerative gingivitis is a destructive, painful inflammatory condition which is, again, more acutely observed in cigarette smokers and tobacco users.

Besides leukoplakia, another type of generalized whitish hue on the buccal mucosa is associated with oral submucous fibrosis. This disease occurs mainly in India and Pakistan and their emigres to the western world and is a chronic, progressive, pre-malignant condition, related to tobacco and betel nut chewing.

Periodontal disease, which includes inflammation of the gums, is one of the most prevalent health problems in the world and is the major cause of tooth loss in the adult population.

Periodontal disease is composed of two entities:
  a) Gingivitis: Inflammation is confined to the gums (gingival tissue).
  b) Periodontitis: The inflammation and infection is present both in the gingiva and in the connective tissue which supports the teeth.

There is initially an inflammation in the local blood vessel walls (vasculitis) which accounts for the most common symptom of bleeding gums. This is accompanied by migration of white blood cells (leucocytes) to help combat the tissue invasion by pathogenic mouth bacteria. In this inflammatory reaction, most cells liberate histamine. Inflammatory (white blood cells) also locally generate countless free radicals and anti-enzyme molecules, both of which contribute to tissue pathology. Collagen production may also then be interfered with due to local Vitamin C deficiency, which contributes to the swelling (edema) and redness (erythema) of gingival tissues.

Chewing tobacco and the areca nut are associated with higher frequencies of periodontal disease, oral submucous fibrosis and oral malignancies. Betel Quid chewing is common in India, Southeast Asia and the South Pacific Islands. Free radical damage induced by these deleterious alkaloids initiate an inflammatory reaction in the oral cavity. Studies in Taiwan reveal that arecoline, the major alkaloid in areca nut interferes with the migration, attachment and growth of human gingival fibroblasts. Arecoline also inhibits these cells' ability to synthesize collagen and all these inhibitory effects have been shown to be associated with an intracellular depletion of L-glutathione (GSH). The repeated and long term exposure to Betel Quid's cytotoxic arecoline and tobacco chewing renders these abusers to periodontal and other oral disease, in part due to losses of the locally vital protective antioxidant and detoxificant, GSH.

Prencipe et al. disclose an anti-bacterial, anti-plaque dentifrice in their U.S. Pat. No. 5,424,059. The '059 patent teaches that plaque can be inhibited and that gingivitis and cavities can be reduced or inhibited by applying a dentifrice in the form of a white water soluble alkaline earth metal polishing agent such as dicalcium phosphate or dimagnesium pyrophosphate used together with an anti-bacterial agent and the polyol, xylitol.

Galiana Arano in WO96/38122 discloses a novel dentifrice composition in the form of a tablet for buccal hygiene which does not require a toothbrush, toothpaste or dental powder. The tablet comprises an abrasive and foaming agent, sugar, one or more lubricants, a fluoride source and sweeteners. It is taught that the cleansing effect of water is obtained from the saliva stimulated by sugars while the mechanical effect of "brushing" is obtained from the granules emanating from the destruction of the tablet.

However, prior attempts to treat gum disease have failed for they have not recognized the role played by free radicals. For example, cigarette tar contains high concentrations of free radicals. The most common oxidants include semiquinone which is in equilibrium with hydroquinones and quinones, particularly in the viscous tar matrix. Many tar extracts are water soluble and reduce oxygen to the superoxide radical which can dismutate to form $H_2O_2$. Importantly, glass-fiber type cigarette filters retain almost all of the tar particles that are larger than 0.1 micron. Thus, the filter acts as a trap for tars and cigarette smoke. There are an inordinately large number of free radicals, greater than $10^{15}$, in each puff of the gas phase of cigarette smoke. While the oxidants in tar are stable, those organic radicals in the gas phase smoke are reactive carbon and oxygen centered radicals with extremely short half-lives. Interestingly, concentrations of free radicals are maintained at high levels for more than ten minutes and tend to increase as tobacco smoke is aged. It is thus considered that these gas phase smoke oxidants are in a steady state as they are both continuously formed and destroyed. The latter reactions are similar to those noted to occur in smog, pointing to the extra noxious stimuli to primary and secondary smokers in polluted environments. In fact, environmental pollution in urban areas such as London, New York, Los Angeles and Mexico City promote gum disease and enhance the damage done to the oral cavity through the consumption of tobacco products. There is now also an established association between gum disease and coronary artery (heart) disease.

It is thus an object of the present invention to provide a gel, paste, gum or lozenge intended to be applied to the gums and teeth of a patient or taken orally as a means of preventing and ameliorating signs and symptoms and complications to the oral-pharyngeal cavity and mouth including the buccal mucosa and gums from damage caused by free radical species generating inflammation in gingival tissues.

These and further objects will be more readily apparent when considering the following disclosure and appended claims.

SUMMARY OF THE INVENTION

The present invention is directed to a gel, paste, gum or lozenge composition and a method of using it for preventing and reducing symptoms of periodontal disease in humans. The composition comprises a carrier and, as active ingredients, an effective amount of reduced glutathione and a source of selenium. Although the present composition is not considered a substitute for toothpaste, it can be applied to the gums in the case of a gel or paste by any well recognized means including the use of a tooth brush and other external applicators.

DETAILED DESCRIPTION OF THE INVENTION

Human gums, are exposed to numerous environmental stimuli. Gums may be damaged by inhaled, ingested or chewed noxious substances, such as tobacco products, and may also be injured by systemic xenobiotics and by endogenous processes, such as inflammatory reactions. Innocent by-standers, the secondary smokers, may equally be adversely affected. Reactive oxidizing species, as induced by inhaled tobacco smoke, ozone and nitrous oxide, are important factors in generating free radicals and inducing inflammatory reactions resulting in the development of periodontal disease. The present invention has now recognized that such periodontal disease resulting from free radical generation can be in large prevented and its symptoms reduced by applying an effective amount of reduced glutathione and a source of selenium in a gel base or paste to the gum surface. The terms gel or paste include compositions wherein medicinal products may be included for specific oro-pharyngeal and odontologic conditions. Examples would include an anti-microbial agent such as those for treatment of oral candidiasis (thrush) or corticosteroid for management of oro-pharyngeal ulcers as both occur commonly in smokers and in patients with AIDS. In these oral condition, and particularly in patients with AIDS and their opportunistic infections, free radical species are indeed pathogenetic. Thus, gels or paste with the compositions of this invention provide significant adjuncts of therapy in the management of oral conditions including gum disease.

It is now recognized that reducing the intracellular levels of GSH in cells increases their sensitivity to oxidant damage. Further, an L-cysteine delivery agent not only enhances endothelial cell GSH concentration, but also protects cells from damage from endogenous hydrogen peroxide. Without being bound to any particular theory, it is noted that reduced glutathione is employed in protecting cells against oxidative stress by itself being oxidized. Thus, L-glutathione must act in combination with other enzyme systems or cellular anti-oxidants in order to be reduced so that it may renew its role as a free radical scavenger. The enzyme glutathione reductase is vital to reduce the glutathione. GSH functions coordinately with the enzyme glutathione peroxidase which requires selenium as a cofactor to exert its biological anti-oxidant function. Selenium compounds, themselves, scavenge oxygen-centered radicals in vivo with reduced glutathione through glutathione peroxidase. By this physiologic method, selenium also functions as an anti-carcinogen. It is believed that selenium-GSH peroxidase catalyzes toxic hydrogen peroxidase in the presence of reduced glutathione. This reaction reduces glutathione to oxidized glutathione (GSSG). In turn, the GSSG is reduced back to GSH by the enzyme GSH reductase thereby maintaining abundant cellular GSH to scavenge free radicals anew.

In summary, the major functions of reduced glutathione (GSH) in protection against lipid peroxidation involve three types of reactions, all inter-related and synergistic in combining non-enzymic scavengers and enzymic and dietary (vitamins C and E) provided antioxidants, to wit:

1. GSH with selenium co-factor glutathione peroxidase eliminate toxic peroxides.

2. GSH reduces oxidized forms of vitamin C which, in turn, maintains vitamin E in its reduced form promoting its metabolic functions. Thus, GSH supports free radical reductions and free radical chain-terminating functions of the two nutrient antioxidants, vitamins C and E.

3. GSH functions through the glutathione S-transferases to detoxify reactive aldehydes created during the process of lipid peroxidation.

Glutathione and selenium act synergistically in vivo as they are both constituents of the same enzymatic system. GSH serves as a specific donor substrate while selenium, provided from alimentary sources or locally from topically administered preparations of selenium, selenoamino acids or selenium yeast extract, provides the prosthetic group for GSH peroxidase. The glutathione and selenium antioxidant functions are intrinsically related since, by keeping a peroxidase in action, the GSH and selenium contribute to the removal of the dismutation product of free oxygen radicals, namely, hydrogen peroxide. In a broad sense, GSH and selenium modulate free radical chains initiated or sustained by hydroperoxides. Selenium is used in the present invention for its role as an antioxidant as well as its anticarcinogenic and antimutagenic properties. Thus, selenium-glutathione complex may lower the level of potentially damaging peroxide radicals that are generated from various carcinogenic promoting chemicals, including tar phase and gas phase tobacco smoke inhaled by-products, particularly side stream smoke, that smoke which flows while the cigarette is being held in between puffs.

Glutathione peroxidase, a group of water soluble enzymes, also catalyze the destruction of both aqueous and membrane-bound hydroperoxides. In dietary selenium deficiency, these enzyme levels are markedly decreased resulting in severe free radical damage to the tissues so involved. The other related antioxidant systems cannot make up for depressed local activity of selenium and selenium dependent enzymes; thus, the importance of providing selenium in these intra-oral antioxidant preparations, as well as ascertaining adequate nutritional supplements.

L-ascorbic acid (vitamin C) or its derivatives can be employed in these compositions primarily for their antioxidant activities. Stabilized vitamin C is employed so that it does not lose its physiological reducing activities because of its high susceptibility to oxidation.

Other components were also investigated as being useful in practicing this invention, for example, the sulphur containing amino acid cysteine, which is one of the three amino acid constituents of the tripeptide antioxidant glutathione (GSH).

Vitamin A is an essential nutrient. Relative vitamin A deficiency may adversely affect the skin and mucous membranes, including the mucosa of the oral cavity and the gingiva. These alterations are reversible on repletion with vitamin A or one of its derivatives.

The present preparations may include flavorings. Flavors may be based on oils of spearmint and peppermint. Other flavoring materials may include menthol, clove, cinnamon, wintergreen, citrus fruits, eucalyptus, aniseed and others commercially available for these flavoring purposes.

Flavors may range in concentrations depending on the product from about 0.1% to about 6.0% by weight of the total composition.

The gels or pastes of this invention may include bicarbonates with thickening agents in a concentration from 0.5% to 5.0% by weight. State of the art thickeners with bicarbonate and zinc salts include, but are not limited to chicle, xanthan, arabic, karaya or tragacanth gums. Alginates, carrageenans and cellulose derivatives such as sodium carboxymethyl, methyl, or hydroxy ethyl compounds are appropriate for the intended preparations; surfactants and abrasives may also be included. Alcohols will otherwise be avoided for their known risk factor for oral cancers. In order to decrease dental cavities and add flavor, without using metabolizable sugars, sweetening agents as saccharin, sodium cyclamate, sorbitol, aspartamane and others may be used in concentrations from 0.005% to 5.0% by weight of the total composition, albeit the polyol xylitol, is preferred. Xylitol has been shown to prevent dental caries and decrease gum disease, in part by reducing the putative oral bacteria, especially Streptococcus mutans.

Gels and dentifrices may contain fluoride anticaries compounds. These fluoride compounds, such as salts of sodium, potassium, calcium, magnesium, stannous and others have been known to protect teeth from developing cavities. Hence, the various fluorinated water systems throughout the country. Fluorides may be present in various amounts in the gels, pastes, gums or lozenges ranging from 0.01% to 3.0% by weight, preferably from 0.05% to 2.0% by weight, most preferably from 0.1% to 1.2% by weight. These sources of stabilized fluoride are taught in U.S. Pat. No. 5,372,802 by Barrows et al., issued Dec. 13, 1994 and which is herein incorporated by reference. These compositions should release from 25 to 2000 PPM of the fluoride ion. The aforementioned patent taught a peroxygen compound, a fluoride and a zinc compound to inhibit the decomposition of the former. Thus, fluorides, optionally may be incorporated in the gels or pastes of these antioxidant preparations to prevent and repair free radical induced gingival diseases.

Other dental antiplaque oral compositions for gels and pastes have been patented with other compounds as optional ingredients. Gaffar in U.S. Pat. No. 5,472,685 issued Dec. 5, 1995, which is also incorporated herein by reference, teaches that the triclosan antimicrobial and antiplaque benefit is enhanced in the presence of a phenolic flavoring agent, such as menthol, eucalyptol or thymol. Antimicrobials may optionally be included in these gels and pastes to help decrease or eliminate the putative bacteria which contribute to the inflammatory reactions in gingivitis and periodontitis.

Lactitol may also be used as a substitute for sucrose in sugar-free compositions. Lactitol is a disaccharide sugar alcohol derived from lactose, highly water soluble and of low hygroscopicity, making it a suitable non-caloric sweetener for use in solid dosage forms. A number of compounds may be added in order to enhance the aromas or tastes of these preparations. These substances may also impart fragrances to the aforementioned. Grapefruit and citrus aroma and flavors have been included in smoking tobacco articles. Methyl phenyl pentanol derivatives have been used to augment and enhance aromas, such as in perfumes and colognes. Schreck patented these derivatives for use in tobaccos and tobacco articles in U.S. Pat. No. 4,458,699, issued Jul. 10, 1994, which is herein incorporated by reference. Floral, green, weedy, fruity, minty, citrusy, oriental and green pepper-like aroma and taste nuances are well known to those skilled in the art of flavors and fragrances for such compositions as in oral sprays, mouthwashes, mouth rinses, gels, dentifrices and other medicinal, nutritional or breath freshener products.

As an optional embodiment, the compositions herein described may also contain zinc or zinc compounds. The state of the art of oral care and hygiene has long recognized the value of zinc to neutralize oral malodor and the value of zinc ions for their anti-plaque and anti-calculus properties. Mouth rinses, mouthwashes, gels and dentifrices will thus complement the properties of the xylitol sweetener in oral and dental preventative care.

Various patents have described different zinc compounds and other complexes in oral compositions. Domke and Bergman taught an aqueous zinc-polyamide complex as a solution for control of halitosis, dental care and to decrease the astringency and metallic taste of zinc in the mouth in U.S. Pat. No. 5,587,147, issued Dec. 24, 1996, which is herein incorporated by reference. This patent discloses previous documents dealing with zinc salts such as zinc chloride, zinc phenol, zinc sulfonate, zinc citrate and other zinc complexes, some of which purportedly also exhibit oral antimicrobial activities. The zinc ion concentrations in these compositions will be at least 0.1% to 3.0% by weight and these will preferably be in an alkaline pH to avoid demineralization of tooth enamel at acid levels. In any event, these aqueous compositions will not have a pH below 6, and preferably about 7.

In order to reduce plaque formation, a number of optional ingredients may be added to the composition of the present invention. This is important for dental plaque is not only a source of dental cavities, but also a significant pathogenetic mechanism for gingivitis and periodontitis. The latter two clinical entities are the main targets of the dentifrice ingredients of the present invention. The oral bacteria and other pathogens associated with dental plaque not only create inflammation with an outpouring of white blood cells (leucocytes) which generate free radical species, but these micro-organisms also secrete enzymes and endotoxins which aggravate inflammation in the gums (gingivitis). This causes the gums to bleed and to lose their toughness that promotes its separation from the teeth, leading to infectious pockets (periodontitis). Thus, optional ingredients in these compositions include abrasives to help reduce plaque, as taught by Rice in U.S. Pat. No. 5,716,601 (Feb. 10, 1998) which is herein incorporated by reference.

The gels and pastes of this invention can also include one or more of the following abrasives at an inclusion range level of 5 to 95% by weight, based upon the weight of the entire composition such as hydrated silica, calcium carbonate, sodium bicarbonate, bicalcium phosphate, bentonite clay or kaolin clay. The preferred level of hydrated silica is 10–30%, the most preferred range is 15–22%.

Another method of application of the gel, paste, gum or lozenge of the present invention is to incorporate the various antioxidants, minerals and amino acids in liposomes or other state of the art encapsulating vehicles, akin to nanospheres, glycospheres and others as used in topical compositions. Liposomes are lecithin spheres that form an oil protective membrane around the putative active ingredients of the composition. These carriers also deliver the active ingredients locally for their preventive and therapeutic functions as well as systemically through buccal mucosal absorption. Unger and co-workers, in U.S. Pat. No. 5,580,575, issued Dec. 3, 1996, which is herein incorporated by reference, have taught therapeutic drug delivery systems comprising gas-filled liposomes which encapsulate the active preparation. Earlier, Chakrabarti and associates, in U.S. Pat. No. 5,380,531, issued Jan. 10, 1995, which is also herein incorporated by reference, disclosed preparations comprising a lipid and a modified peptide for incorporation into liposomes. In addition, Knight et al. (U.S. patent '388) has taught small particle aerosol liposomes and liposome combinations for medical delivery uses.

As an example of the present invention, a paste can be formulated having the following ingredients.

| INGREDIENTS | % BY WEIGHT |
|---|---|
| glycerol | 32.0 |
| magnesium carbonate | 3.5 |
| sodium fluoride | 0.10 |
| zinc acetate | 0.50 |
| L-glutathione | 0.1 |
| L-selenomethionine | 0.05 |
| ascorbic acid | 1.50 |
| N-acetyl cysteine | 0.10 |
| vitamin E | 0.25 |
| benzalkonium chloride | 0.10 |
| xylitol as sweetener | 0.25 |
| polyvinyl pyrrolidone | 7.5 |
| coloring agent | 0.20 |
| flavor, as peppermint | 0.20 |

Ascorbic acid or ascorbyl palmitate may be incorporated in protective liposomes, as well as the glutathione and cysteine, N-acetyl cysteine and/or other amino acids employed in dentifrice formulations. As noted, whitening agents such as sodium monofluorophosphate and antimicrobials may also be comprised in these dental formulations.

Further, the following gel is exemplary of the present invention.

| INGREDIENTS | % BY WEIGHT |
|---|---|
| glycerin | 42.0 |
| poloxamer | 18.0 |
| xylitol | 3.5 |
| ascorbic acid | 2.0 |
| sodium lauryl sulfate | 1.2 |
| natural peppermint oil | 1.0 |
| alpha-tocopherol | 0.75 |
| green tea | 0.5 |
| calcium lactate | 0.25 |
| selenomethionine | 0.20 |
| sodium fluoride | 0.20 |
| L-glutathione | 0.10 |
| coloring agent | 0.10 |
| deionized water | balance |

In addition, the following composition is characteristic of a suitable lozenge.

| ACTIVE INGREDIENTS: | |
|---|---|
| L-glutathione | 50 mg. |
| N-acetyle-l-cysteine | 50 mg. |
| selenium (selenomethionine) | 70 mg. |
| alpha lipoic acid | 25 mg. |
| vitamin A acetate | 5000 I.U. |
| ascorbic acid | 180 mg. |
| alpha tocopheryl acetate | 60 I.U. |
| copper lysinate | 2 mg. |
| manganese picolinate | 15 mg. |
| zinc picolinate | 15 mg. |
| OPTIONAL ANTIOXIDANTS: | |
| grape seed extract | 25 mg. |
| green tea extract | 50 mg. |
| coenzyme Q10 | 50 mg. |
| SUGAR SUBSTITUTES: | |
| xylitol or lactilol | |

What is claimed is:

1. A gel or paste composition for oral application to human gums to reduce symptoms of gum disease, said composition comprising a gel or paste-based carrier and, as active ingredients, an effective amount of reduced glutathione and a source of selenium to reduce said symptoms of gum disease.

2. The gel or paste composition of claim 1 wherein said source of selenium comprises a member selected from the group consisting of elemental selenium, a selenoamino acid, a selenium yeast extract and a selenium chelate.

3. The gel or paste composition of claim 2 wherein said selenoamino acid comprises a member selected from the group consisting of selenomethionine and selenocystine.

4. The gel or paste composition of claim 1 further comprising vitamin C as ascorbic acid or as a derivative of ascorbic acid.

5. The gel or paste composition of claim 1 further comprising vitamin E as alpha tocopherol.

6. The gel or paste composition of claim 1 further comprising superoxide dismutase.

7. The gel or paste composition of claim 1 further comprising vitamin A.

8. A method of reducing symptoms of periodontal disease in humans, said method comprising applying to human gums a gel or paste including, as active ingredients, an effective amount of reduced glutathione and a source of selenium.

9. The method of claim 8 wherein said source of selenium comprises a member selected from the group consisting of elemental selenium, a selenoamino acid, a selenium yeast extract and a selenium chelate.

10. The method of claim 9 wherein said selenoamino acid comprises a member selected from the group consisting of selenomethionine and selenocysteine.

11. The method of claim 8 further comprising applying vitamin C in said gel or paste as ascorbic acid or as a derivative of ascorbic acid to human gums.

12. The method of claim 8 further comprising applying vitamin E in said gel or paste as alpha tocopherol the human gums.

13. The method of claim 8 further comprising applying superoxide dismutase to human gums in said gel or paste.

14. The method of claims 8 further comprising applying vitamin A in human gums in said gel or paste.

15. The gel or paste of claim 1, further comprising a flavorant.

16. The gel or paste of claim 15 wherein said flavorant is xylitol.

17. The gel or paste of claim 1 wherein said active ingredients are encapsulated in a liposome.

18. The gel or paste of claim 1 further comprising an abrasive.

19. The gel or paste of claim 18 wherein said abrasive is a member selected from the group consisting of hydrated silica, calcium carbonate, sodium bicarbonate, dicalcium phosphate, bentonite clay and kaolin clay.

20. The gel of claim 19 further comprising fluoride.

21. A gum composition for oral application to human gums to reduce symptoms of gum disease, said composition comprising a gum-based carrier and, as active ingredients, an effective amount of reduce glutathione and a source of selenium.

22. A lozenge composition for oral application to human gums to reduce symptoms of gum disease, said composition comprising a lozenge-based carrier and, as active ingredients, an effective amount of reduce glutathione and a source of selenium.

23. The gel or paste composition of claim 1 further comprising an amino acid, cysteine.

24. The method of claim 8 further comprising applying an amino acid cysteine in said gel or paste to human gums.

\* \* \* \* \*